United States Patent
Tanaka

[11] Patent Number: 5,969,272
[45] Date of Patent: Oct. 19, 1999

[54] SAMPLE SUCKING PIPE AND METHOD FOR MANUFACTURING SAME

[75] Inventor: Shuichi Tanaka, Kobe, Japan

[73] Assignee: Sysmex Corporation, Kobe, Japan

[21] Appl. No.: 08/815,011

[22] Filed: Mar. 14, 1997

[30] Foreign Application Priority Data

Mar. 14, 1996 [JP] Japan .................................. 8-057580
Mar. 6, 1997 [JP] Japan .................................. 9-051936

[51] Int. Cl.⁶ .................................................. G01N 35/02
[52] U.S. Cl. .......................................................... 73/864.24
[58] Field of Search ........................ 73/863.31–863.33, 73/864.01, 864.21–864.25; 422/100; 138/115

[56] References Cited

U.S. PATENT DOCUMENTS

| | | |
|---|---|---|
| 3,804,097 | 4/1974 | Rudie . |
| 3,885,438 | 5/1975 | Harris, Sr. et al. . |
| 4,320,761 | 3/1982 | Haddad . |
| 4,475,411 | 10/1984 | Wellerfors . |
| 4,958,901 | 9/1990 | Coombs . |
| 5,315,887 | 5/1994 | Heitel . |
| 5,318,359 | 6/1994 | Wakatake . |
| 5,322,510 | 6/1994 | Lindner et al. . |

FOREIGN PATENT DOCUMENTS

| | | |
|---|---|---|
| 58-76765 | 9/1983 | Japan . |
| 6-30203 | 8/1994 | Japan . |
| 7-14894 | 4/1995 | Japan . |
| 9101007 | 1/1991 | WIPO . |

*Primary Examiner*—Robert Raevis

[57] ABSTRACT

There is disclosed a sample sucking pipe the manufacture of which is easy and which is also advantageous costwise, whose strength is relatively great and whose usage life is long and with which it is possible to prevent the occurrence of trouble such as dust clogging and sample leakage. There is also disclosed a method for manufacturing the same. A sample sucking pipe P is for sucking samples of blood contained in a sample vessel T through a rubber cap C, and is made up of a sucking pipe 10, a venting pipe 20 and a holding piece 30. The pipes 10, 20 are made of the same stainless steel. The holding piece 30 is made of polyacetal resin. The pipes 10, 20 are disposed parallel with each other with their tip ends aligned and then integrated by welding carried out along the tip end portion of the contacting part of their walls. A sucking opening 13 and a venting opening 23 are provided in the walls of the pipes 10, 20 respectively and, on the tip end side of these openings, the pipe passageways of the pipes 10, 20 are closed with rod-like members made of the same material as the pipes.

8 Claims, 10 Drawing Sheets

SAMPLE SUCKING PIPE AND METHOD FOR MANUFACTURING SAME

BACKGROUND OF THE INVENTION

This invention relates to a sample sucking pipe for sucking a liquid sample from inside a vessel, and more particularly to a sample sucking pipe for example built into a sample sucking device constituting a part of a blood analyzing apparatus and used for collecting a liquid sample contained in a sealed vessel and carrying out a predetermined analysis thereof.

DESCRIPTION OF THE RELATED ARTS

Conventionally, as sample sucking pipes for sucking a liquid sample from inside a sample vessel sealed with a rubber cap or plug or the like, there have been those having a pipe for sucking a sample and a pipe for carrying out venting during sample sucking and used with both of the pipes being thrust through the rubber cap.

That is, as disclosed in Japanese Unexamined Patent Publication No. SHO 58(1983)-76765, there have been sample sucking pipes (sucking needles) constituting a main element of a sample supply apparatus and having a coaxial structure wherein a sucking pipe (a pipe having a central through-hole) and a venting pipe (a pipe having a second through-hole) are provided coaxially and sucking of a sample is carried out using the central through-hole and venting is carried out using the second through-hole.

Also, as sample dispensing pipes for dispensing liquid samples into sample vessels sealed with a rubber cap or plug or the like, there have been those having a dispensing pipe for dispensing a sample and a venting pipe for carrying out venting during sample dispensing and used with both of the pipes being thrust through the rubber cap.

That is, as disclosed in Japanese Utility Model Publication No. HEI 6(1994)-30203, there have been sample dispensing pipes (liquid dispensing needles) made by integrally molding a dispensing pipe (a pipe having a liquid delivery hole) and a venting pipe (a pipe having an air venting hole) out of resin in the shape of a rod.

The former of these, the sample sucking pipe, is difficult to manufacture and also disadvantageous costwise because it comprises two pipes provided coaxially. The latter, the sample dispensing pipe, is not as strong as a metal pipe because it is molded integrally using resin.

Also, there are the following problems in both of these types of pipe. That is, because the external diameter of the overall pipe is large in both cases, there is a large amount of friction caused between the pipe and a rubber cap (or plug or the like) when the pipe is thrust through the rubber cap, and not only is there a likelihood of the outer surface of the pipe wearing but also a large force is required to pierce the cap and an excessive force acts on the pipe. Because these pipes pierce rubber caps or the like many times when they are used for sample sucking in a sample analyzing apparatus, durability is required of the pipes.

However, particularly in the case of the sample dispensing pipe, there has been a problem that it wears severely and its usage life is short because it is made of resin. Also, because the external diameter of the overall pipe is large in both cases, there has been a problem that much dust is produced from the rubber cap or the like during piercing and it tends to clog the pipe. Furthermore, after the pipe is removed, a hole remains in the rubber cap or the like and sample leaks out through this hole.

SUMMARY OF THE INVENTION

The present invention provides a sample sucking pipe the manufacture of which is easy and which is also advantageous costwise, whose strength is relatively great and whose usage life is long, and with which it is possible to prevent the occurrence of trouble such as dust clogging and sample leakage.

More particularly, the invention provides a sample sucking pipe comprising: a metal pipe for sucking having a closed (blocked) portion at the tip end of its pipe passageway and a non-closed (non-blocked) portion of its pipe passageway serving as a sample passageway and having in its wall a sucking opening communicating with the sample passageway; and a metal pipe for venting having a closed portion at the tip end of its pipe passageway and a non-closed portion of its pipe passageway serving as a venting passageway and having in its wall a venting opening communicating with the venting passageway, wherein the two pipes are disposed parallel to each other and integrated by bonding.

Pipes made of a metal material such as stainless steel or nickel-titanium alloy are for example used as the sucking pipe and the venting pipe.

The cross-sectional shapes of these pipes are normally circular or elliptical, in consideration of the ease with which they can be thrust through a rubber cap or plug or the like constituting a sealing member of a sample vessel. Alternatively, however, they may be square or of another shape.

Here, various types of welding or brazing, or adhesion with adhesive can be suitably selected and used as the method by which the two pipes are bonded. The locations bonded are not particularly limited.

However, in consideration of the strength of the sample sucking pipe, at least the wall surfaces of the tip end portions are bonded.

As a method for carrying out closing of the tip end portions of the pipe passageways of the pipes, known methods such as various types of welding or brazing, or adhesion with adhesive can be used. However, the method of inserting a metal rod-like member into the pipe passageway at the tip end of each of the unclosed pipes is more preferable. Here, from the point of view of placing importance to manufacturability and strength and so on and from the point of view of preventing the occurrence of electrolytic corrosion, preferably the same material is used for the pipes and the rod-like members so that the sample sucking pipe is made out of a single type of metal.

DETAILED DESCRIPTION OF THE PREFERRED EMBODIMENTS

Figure 1:
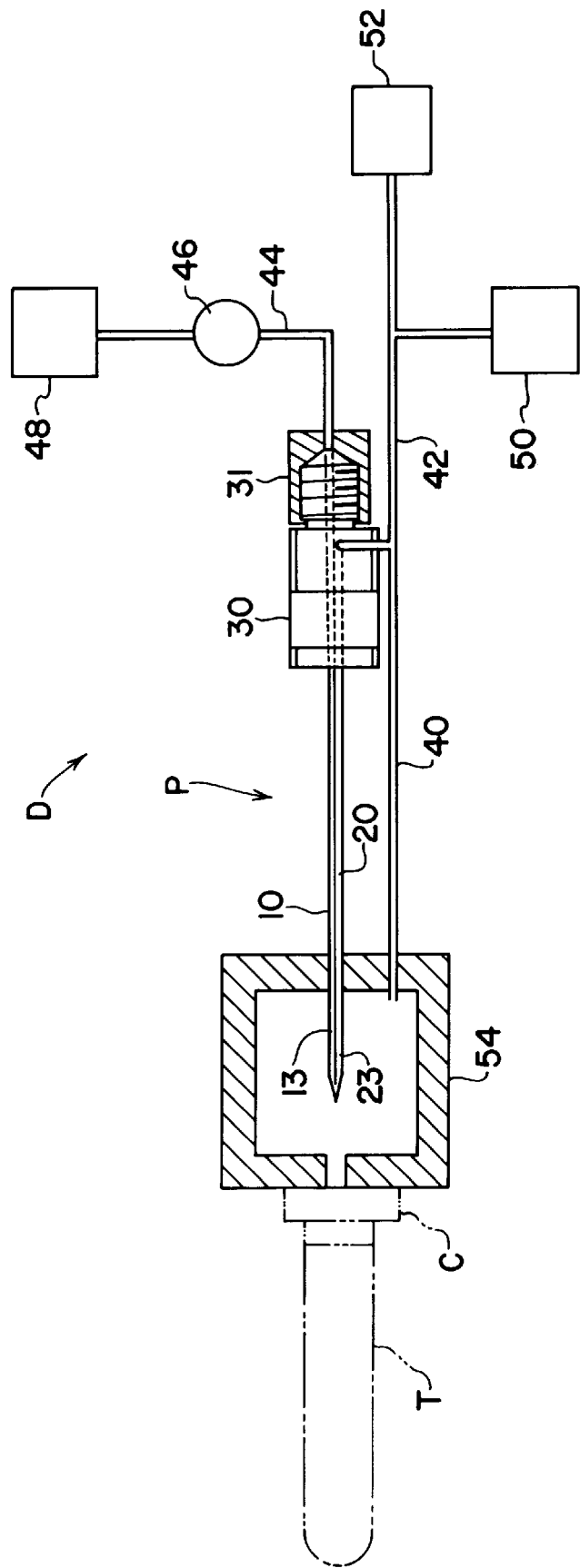
FIG. 1 is a schematic construction view of a sample sucking device including a sample sucking pipe of a preferred embodiment of the invention.

In a sample sucking pipe according to the invention, preferably diagonal cut surfaces for piercing are provided on the closed portions of the capillary pipes and these two diagonal cut surfaces are disposed back-to-back. The shape of each diagonal cut surface is substantially elliptical when the cross-sectional shape of the respective capillary pipe is substantially circular or substantially elliptical, and is rectangular when the cross-sectional shape of the respective capillary pipe is square. Here, 'back-to-back' is a concept which, besides the state of the tips of the capillary pipes (the tips of the diagonal cut surfaces) being in contact, includes the state of the tips of the capillary pipes being almost in contact.

When the diagonal cut surfaces of the capillary pipes are substantially elliptical, (i.e. when the cross-sectional shape of each of the capillary pipes is substantially circular or substantially elliptical), the sucking opening in the capillary sucking pipe and the venting opening in the capillary venting pipe are preferably disposed in locations off the generatrices of the capillary pipes intersecting with ends of the major axes of the (substantially elliptical) diagonal cut surfaces of the capillary pipes. This is due to the following reason. Because relatively much dust is produced from the rubber cap or plug or the like at the locations of the two back-to-back diagonal cut surfaces when the sample sucking pipe is thrust through the rubber cap or the like. This dust, which moves rearward on the generatrices of the capillary pipes intersecting with ends of the major axes of the diagonal cut surfaces along with the forward movement of the sample sucking pipe, should be prevented from clogging the sucking opening and the venting opening.

When the diagonal cut surfaces of the capillary pipes are substantially elliptical, the sucking opening and the venting opening still more preferably are disposed on generatrices of the capillary pipes intersecting with ends of the minor axes of the (substantially elliptical) diagonal cut surfaces of the capillary pipes. This is to more certainly prevent the above-mentioned dust from clogging the sucking opening and the venting opening.

In integrating the two capillary pipes according to the present invention, it is preferable to use two triangular prism-like members formed of the same material as that of the two capillary pipes and each including a concave curved surface having substantially the same curvature as a side wall of one of the capillary pipes and a concave curved surface having substantially the same curvature as a side wall of the other of the capillary pipes, the two curved surfaces being adjacent to each other at a ridgeline. It is further preferable to bond the two capillary pipes and the two triangular prism-like members together so that a transversal cross section of at least the tip end portion of the sample sucking pipe is shaped substantially like an ellipse when the sample sucking pipe is completed.

In this case, the two triangular prism-like members are formed, for example, by a process of drawing a rod-like material using a die. The two triangular prism-like members are arranged so as to fill the two V-shaped concave portions formed in the contacting part of the two capillary pipes when the two capillary pipes are arranged in parallel and in close contact with each other. Namely, the two triangular prism-like members are arranged so as to be in close contact with sidewalls in the concave portions of the capillary pipes with the ridgeline thereof facing each other.

Such sample sucking pipes are advantageously manufactured by the following process. First, two metal capillary pipes and two metal triangular prism-like members are arranged in parallel and in close contact with each other. The two capillary pipes serve for sucking and venting. Then, the two capillary pipes and the two triangular prism-like members are integrated together by contacting an electrode with each of the two triangular prism-like members and performing an electric resistance welding (for example, a spot welding or a seam welding) from both sides of the contacted portion. Subsequently, a sucking opening or a venting opening is formed at a sidewall of a tip end portion of each of the two capillary pipes. Next, a tip end portion of each capillary pipe is closed by inserting a metal rod-like member into a tip end passageway of each of the two capillary pipes. Subsequently, a diagonal cut surface for piercing the capillary pipes is formed by grinding the closed tip end portions of the two capillary pipes. Lastly, an anti-abrasion film is formed on at least the tip end portion of the sidewalls of the integrated two capillary pipes and two triangular prism-like members.

A preferred embodiment of the invention will now be described with reference to the accompanying drawings. However, the invention is not limited by this preferred embodiment.

FIG. 1 is a schematic construction view of a sample sucking apparatus D including a sample sucking pipe P of a preferred embodiment of the invention. In FIG. 1, the sample sucking apparatus D is mainly made up of the sample sucking pipe P, a venting pipe 40, a connecting pipe 42, a suction pipe 44, a volume regulating device 46, a suction syringe 48, a cleaning liquid supply pump 50, an air pressure source 52, and a cleaning tank 54. The sample sucking pipe P and the suction pipe 44 are connected by a holding piece 30 and a holder 31 being screwed together.

Figure 2:
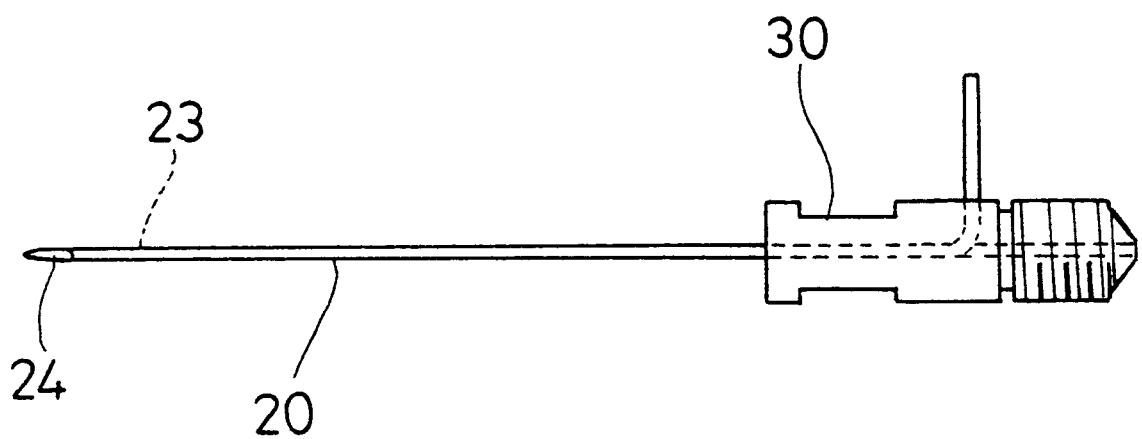
FIG. 2 is a bottom view of the sample sucking pipe of FIG. 1.
Figure 3:
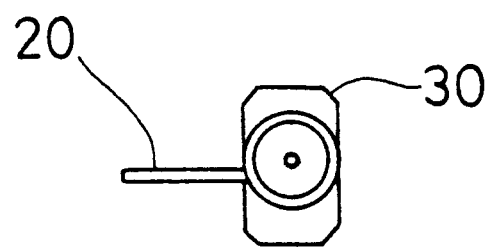
FIG. 3 is a right side view of the sample sucking pipe of FIG. 1.
Figure 4:
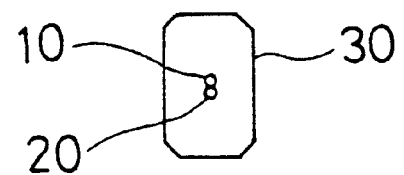
FIG. 4 is a left side view of the sample sucking pipe of FIG. 1.

The sample sucking pipe P is for sucking and collecting, through a rubber cap C fitted to a sample vessel T, a blood constituting a liquid sample contained in the sample vessel T. As shown in FIG. 2 through FIG. 4, the sample sucking pipe P is made up of a sucking capillary pipe 10 for sucking the blood, a venting capillary pipe 20 for carrying out venting during blood sucking and the holding piece 30 for holding these two capillary pipes 10, 20.

The capillary pipe 10 and the capillary pipe 20 are cross-sectionally circular pipes both made of the same metal, which in this preferred embodiment is stainless steel. The holding piece 30 is a member made of polyacetal resin and shaped like a rectangular parallelopiped. The capillary pipe 10 and the capillary pipe 20 are disposed in parallel with each other with their tip ends (left ends) aligned and then integrated by welding carried out along the tip end portion of the contacting part of their walls. Their base ends (right ends) and portions in the vicinity of their base ends are embedded in the holding piece 30. The capillary pipe 10 and the capillary pipe 20 both have an external diameter of about 0.8 mm, an internal diameter of about 0.5 mm, and a length of about 50.0 mm in the part extending from the holding piece 30 to the tip end.

Figure 5:
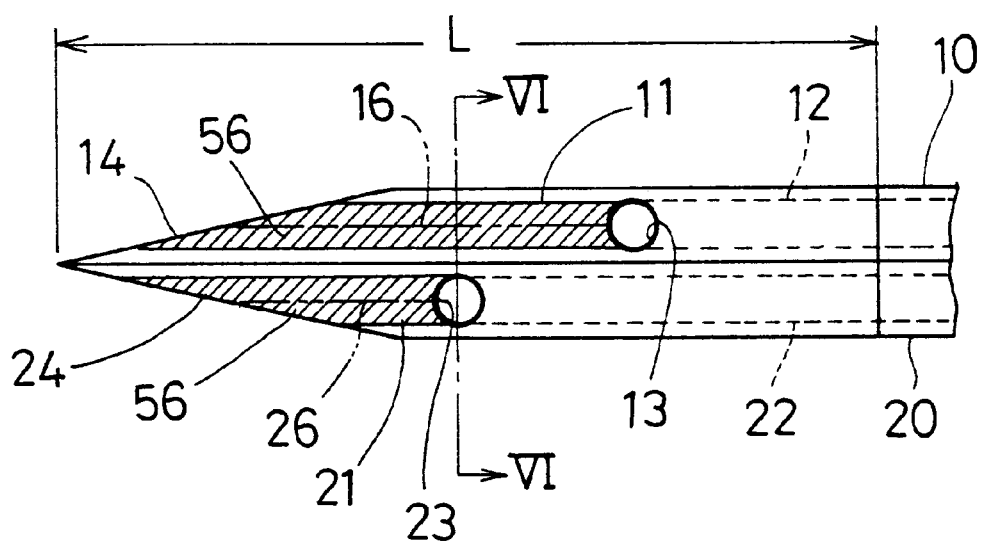
FIG. 5 is an enlarged front view of the tip end of the sample sucking pipe of FIG. 1.

The capillary pipe 10 and the capillary pipe 20, as shown enlarged in FIG. 5, are both provided with a closed portion 11, 21 formed by closing the tip end of the pipe passageway. The non-closed portions of their pipe passageways respectively constitute a sample sucking passageway 12 for sucking a blood constituting a sample and a venting passageway 22 for carrying out venting during sample sucking.

Figure 6:
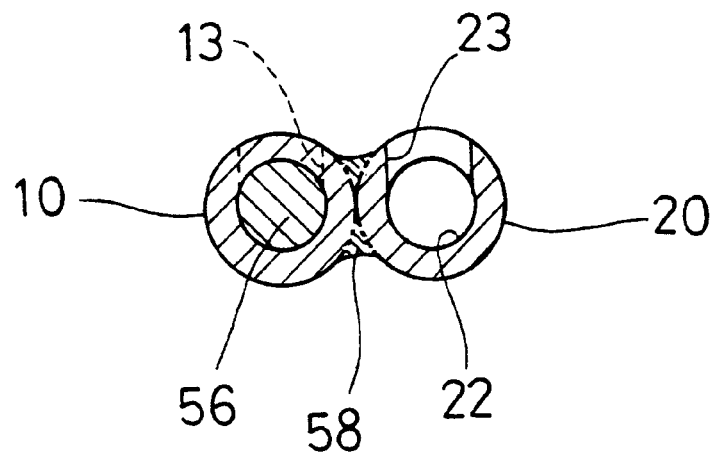
FIG. 6 is a sectional view along the line VI—VI of FIG. 5.

As shown in FIG. 5 and FIG. 6, a circular sucking opening 13 communicating with the sample sucking passageway 12 is provided in the wall of the sucking capillary pipe 10 and a circular venting opening 23 communicating with the venting passageway 22 is provided in the wall of the venting capillary pipe 20. The reference numeral 58 in FIG. 6 denotes a part created by the above-mentioned welding carried out on the capillary pipes 10, 20.

The closed portions 11, 21 of the capillary pipes 10, 20 are formed by inserting rod-like members (pins) 56, 56 made of stainless steel, which is the same material as that of the capillary pipes 10, 20, into the tip ends of the pipe passageways of the unclosed capillary pipes 10, 20 as far as the openings 13, 23 and by bonding.

This bonding was carried out by cold fitting of the rod-like members 56, 56. That is, first the rod-like members 56, 56 were placed in industrial alcohol and dry ice was crushed and put into the alcohol. When this was done, it was possible to insert the rod-like members 56, 56 into the tip end pipe passageways of the unclosed capillary pipes 10, 20 easily because the temperature fell to −40° C. to −70° C. in a few minutes and the diameter of the rod-like members 56, 56 contracted. When they returned to room temperature, the rod-like members 56, 56 tried to return to their initial diameter and, as a result, the rod-like members 56, 56 exerted a pressure on the walls of the tip end pipe passageways of the capillary pipes 10, 20 and were thereby bonded.

Substantially elliptical diagonal cut surfaces 14, 24 for enabling the capillary pipes 10, 20 to pierce a rubber cap or plug or the like are provided on the closed portions 11, 21 of the capillary pipes 10, 20. These two diagonal cut surfaces 14, 24 have the same shape and size as each other and are disposed back-to-back.

Figure 7:
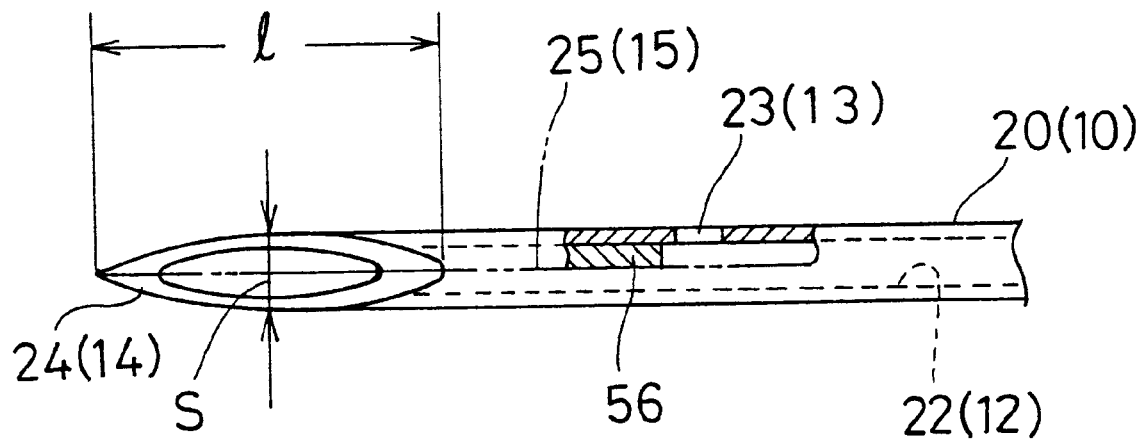
FIG. 7 is an enlarged front view of the tip ends of the capillary pipes constituting the sample sucking pipe of FIG. 1.

When these diagonal cut surfaces 14, 24 are regarded as ellipses with major axis l, minor axis s as shown in FIG. 7, the sucking opening 13 and the venting opening 23 are disposed in locations off the generatrices 15, 25 of the respective capillary pipes 10, 20 intersecting with ends of the major axes l. That is, these openings 13, 23, as shown in FIG. 5, are so provided that the centers of the openings are positioned on the generatrices 16, 26 of the capillary pipes 10, 20 intersecting with ends of the minor axes s.

In general, a generatrix can be defined as a virtual line which, as a component is combined with other component vertical lines to form a surface (such as a conical surface or as in the preferred embodiment a cylindrical or pipe surface). Thus, the generatrices 15, 25, and 16, 26 are virtual pipe surface lines having locations defined by their intersecting points with the elliptical cut surfaces (i.e. the ends of the major and minor ellipse axes). In turn, locations of sucking and venting openings 13 and 23 are defined with reference to the generatrices 15, 25 and 16, 26.

The reason for this is as follows. When the sample sucking pipe P is thrust through the rubber cap C of the sample vessel T, there is a strong tendency for dust of the rubber cap C, much of which is produced at the locations of the two back-to-back diagonal cut surfaces 14, 24 of the capillary pipes 10, 20, to move rearward on the generatrices 15, 25 of the capillary pipes 10, 20 along with the forward movement of the sample sucking pipe P. Therefore, if the sucking opening 13 and the venting opening 23 are disposed on the generatrices 16, 26 of the respective capillary pipes 10, 20, this dust can be certainly prevented from clogging the openings 13, 23.

The tip end part shown with the length L in FIG. 5 of the outer surfaces of the capillary pipes 10, 20 is coated with a film having a superior anti-abrasion and anti-corrosion property. That is, a titanium film is formed there by means of ion-plating. As a result of providing this kind of film, the length L part of the outer surfaces of the capillary pipes 10, 20 is given a higher hardness than other parts and wears less easily when piercing the rubber cap C.

Next, the sample sucking pipe Q according to another embodiment of the invention and the method for manufacturing the same will be hereafter explained with reference to FIGS. 8 to 16.

Contacting Step

Figure 8:
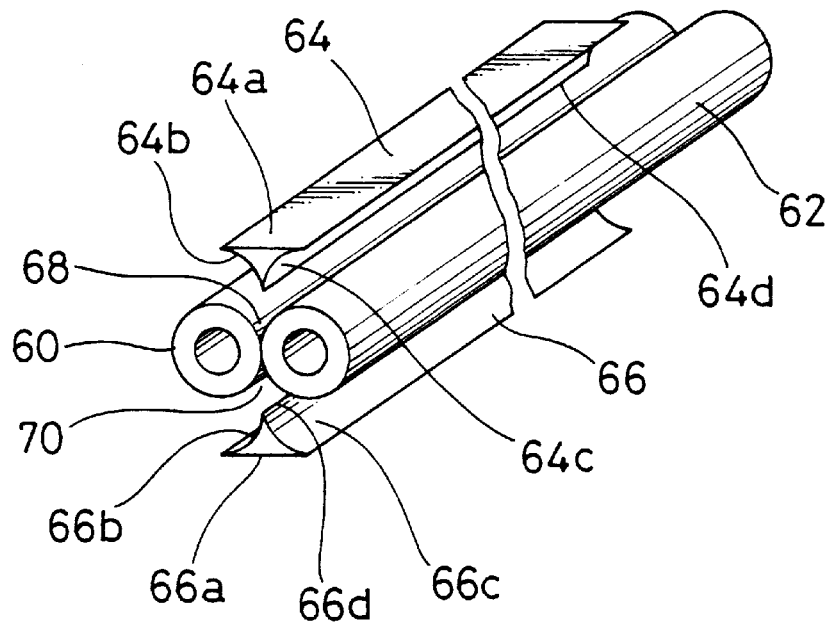
FIG. 8 is a construction view of a midway state of a contacting step in manufacturing a sample sucking pipe according to another preferred embodiment of the invention.

Referring to FIG. 8, two capillary pipes 60, 62 made of stainless steel and two triangular prism-like members 64, 66 made of the same material as that of the capillary pipes are prepared. The capillary pipes 60, 62 each have a length of about 75 mm, an outer diameter of about 0.8 mm, and an inner diameter of about 0.5 mm. The triangular prism-like members 64, 66 are formed by a process of drawing a rod-like material employing a die mounted to a line drawer so that the prism-like members may have substantially a shape of an equilateral triangle in its transversal cross section. Each of the triangular prism-like members 64, 66 has a length of about 50 mm and includes a plane 64a, 66a and two concave curved surfaces 64b, 64c, 66b, 66c having substantially the same curvature as the sidewalls of the two capillary pipes 60, 62, the two curved surfaces 64b, 64c, 66b, 66c being adjacent to each other via a ridgeline 64d, 66d.

Figure 9:
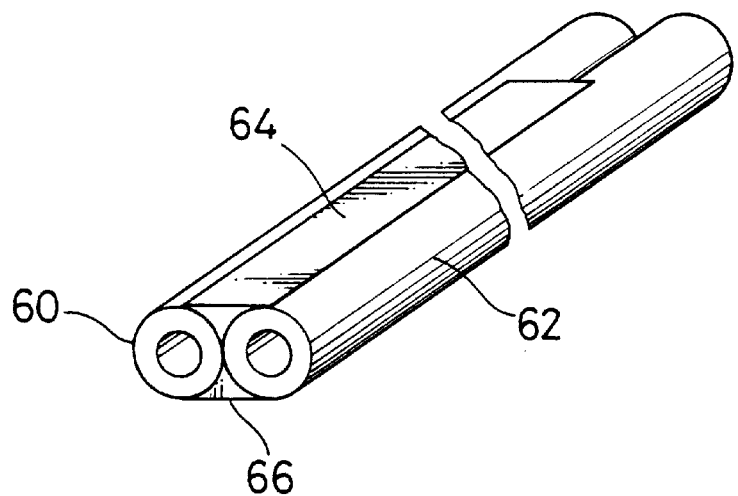
FIG. 9 is a construction view of the contacting step in manufacturing the sample sucking pipe of FIG. 8.

First, as shown in FIG. 8, the two capillary pipes 60, 62 are arranged in parallel and in close contact with each other at the sidewalls with the tip end portions thereof being aligned. Then, as shown in FIG. 9, the two triangular prism-like members 64, 66 are arranged along and in close contact with the sidewalls of the two capillary pipes 60, 62 with the ridgelines 64d, 66d facing each other. Namely, the two triangular prism-like members 64, 66 are arranged so as to fill the two V-shaped concave portions 68, 70 formed in the contacting part of the two capillary pipes when the two capillary pipes 60, 62 are arranged in parallel and in close contact with each other.

Figure 10:
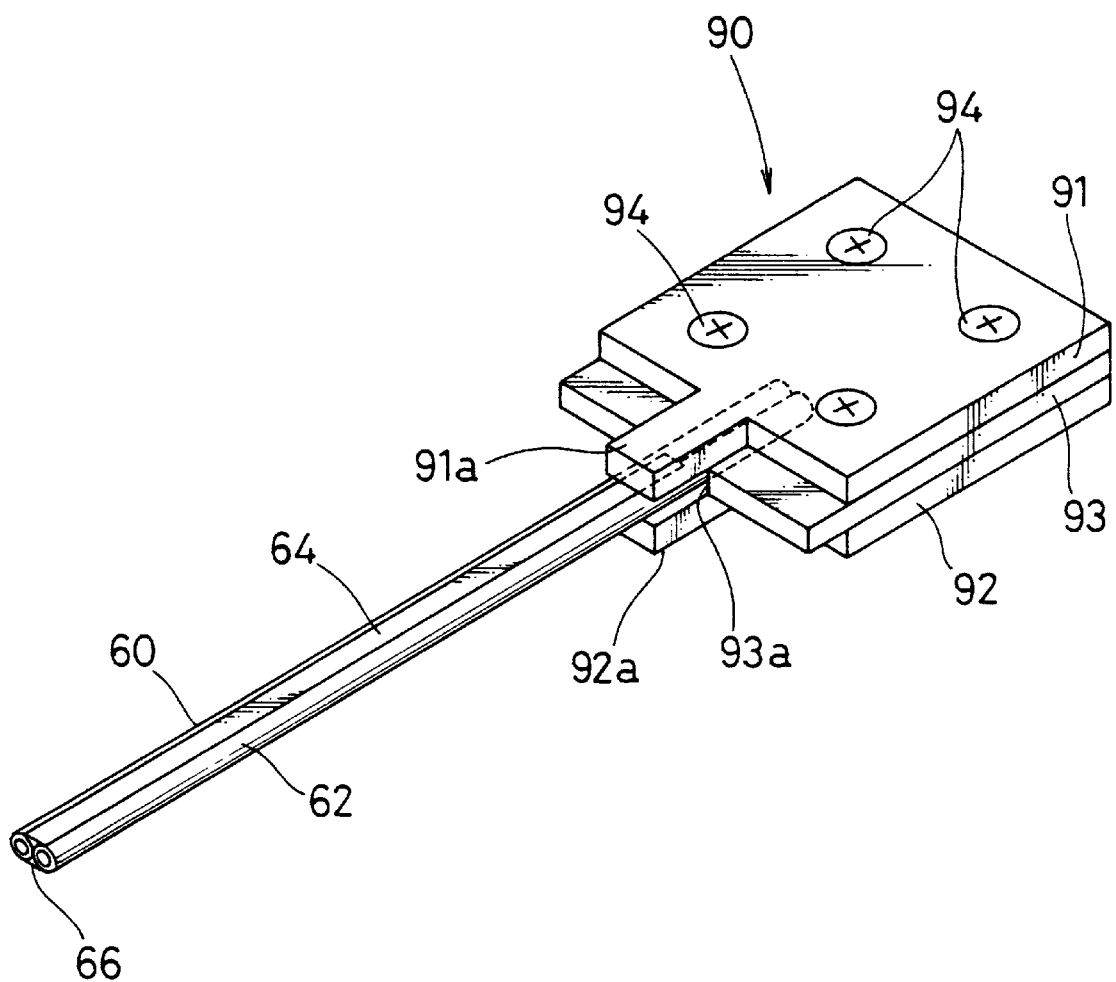
FIG. 10 is a construction view of the contacting step in manufacturing the sample sucking pipe of FIG. 8.

The close arrangement was carried out using a fixing device 90 shown in FIG. 10. Namely, the fixing device 90 is formed by integrating an upper plate 91, a lower plate 92, and an inner plate 93, each having substantially a square shape, by means of four screw members 94. Each of the upper plate 91 and the lower plate 92 includes a protruding portion 91a, 92a having a width of about 4 mm. The inner plate 93 includes a holding portion 93a. The holding portion 93a has a width of about 1.7 mm, a height of about 0.9 mm, and a depth which is equal to that of the inner plate 93.

The above close contacting process was carried out by inserting the base ends of the two capillary pipes 60, 62 and the two triangular prism-like members 64, 66 into the holding portion 93a of the fixing device 90 to a certain length.

Welding Step

Figure 11:
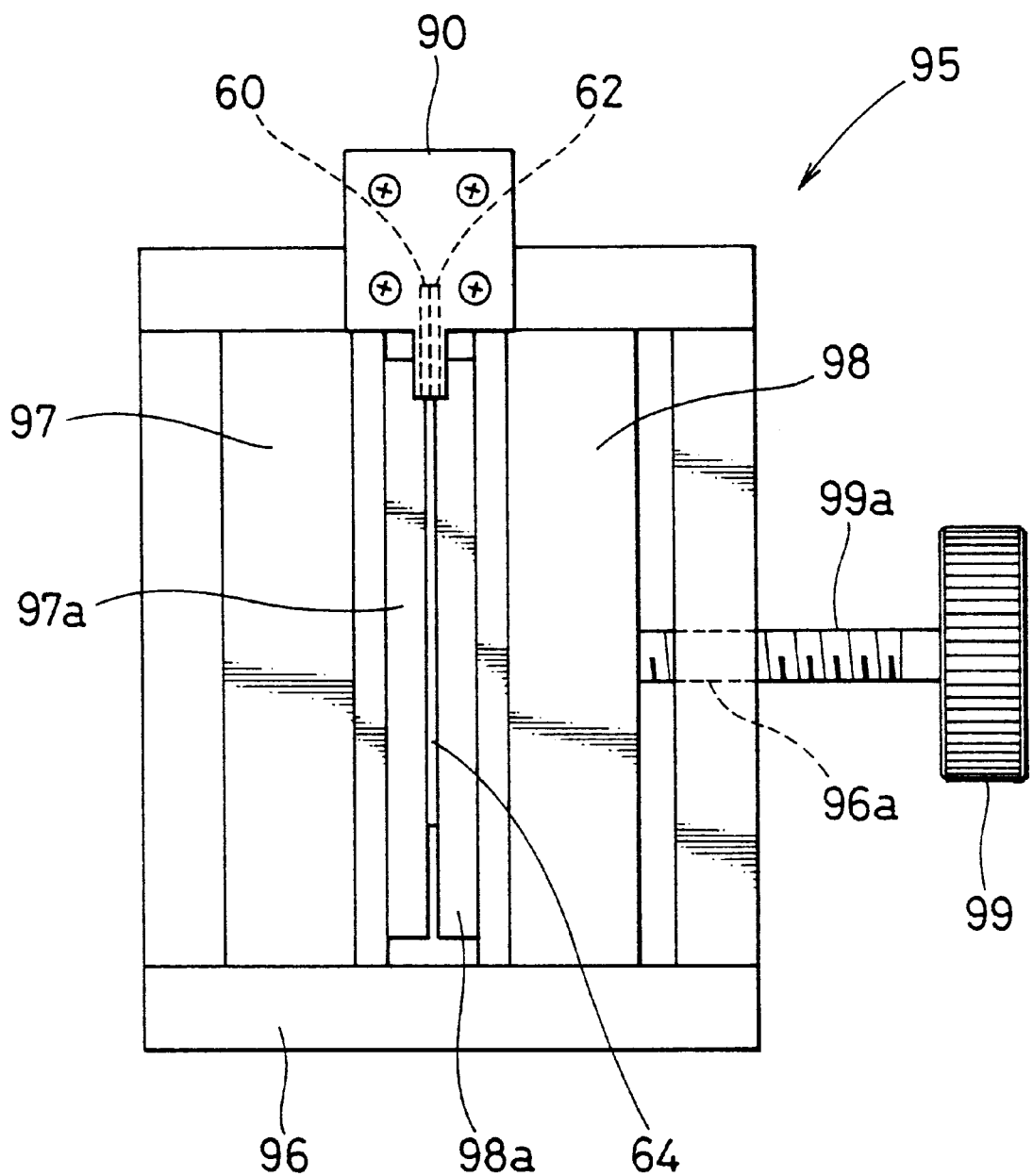
FIG. 11 is a construction view of the contacting step in manufacturing the sample sucking pipe of FIG. 8.

Then, the two capillary pipes 60, 62 and the two triangular prism-like members 64, 66 arranged in close contact by the fixing device 90 are held and gripped from right and left sides by means of a vise 95 shown in FIG. 11. Namely, the vise 95 includes a frame 96 having a box-like shape in its plan view, a left gripping member 97 disposed in a fixed manner in the inside of the frame 96, a right gripping member 98 disposed in a movable manner in the inside of the frame 96, and an operation member 99 connected to the right gripping member 98. The operation member 99 includes a male screw portion 99a that engages with a female screw portion 96a disposed in the frame 96. The rotation of the male screw portion 99a allows the right gripping member 98 to move to the right or to the left. The two gripping members 97, 98 each have a gripping portion 97a, 98a.

Figure 12:
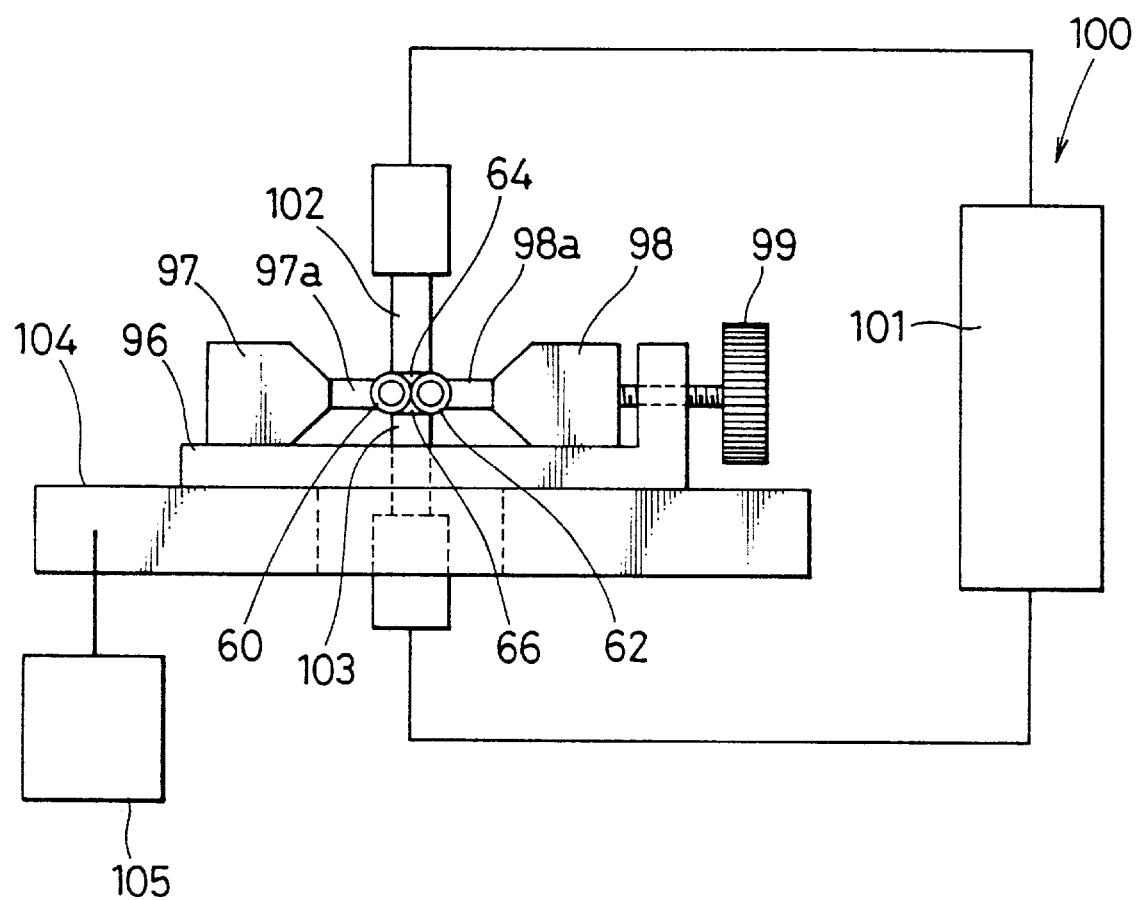
FIG. 12 is a construction view of the welding step in manufacturing the sample sucking pipe of FIG. 8.

The two capillary pipes 60, 62 and the two triangular prism-like members 64, 66 arranged in close contact by the fixing device 90 and held by the vise 95 are then subjected to spot welding by means of a spot welding apparatus 100 shown in FIG. 12. Namely, the spot welding apparatus 100 is constructed mainly with a main welding body 101, a pair of upper and lower electrodes 102, 103 connected to the main welding body 101, a movable table 104 which can be moved in forward and backward directions (i.e. the directions perpendicular to the paper in FIG. 12), and a driving section 105 for moving the movable table 104.

In this spot welding process, the movable table 104 is moved intermittently in a forward direction (the direction of the front surface of the paper in FIG. 12) after the vise 95 holding the two capillary pipes 60, 62 and the two triangular prism-like members 64, 66 is fixed at a predetermined position by means of screws to an upper surface of the movable table 104. In association with the movement of the movable table 104, the electrodes 102, 103 are intermittently pressed onto the surfaces 64a, 66a of the two triangular prism-like members 64, 66 arranged in close contact with the two capillary pipes 60, 62 and are charged with electricity so as to carry out the predetermined spot welding.

The welding condition of the spot welding was as follows. The charging voltage: 270 V, the welding current: 1.6 A/msec, the welding pitch: 0.2 mm, the welding location: within 50 mm from the tip end portion of the two capillary pipes 60, 62 and the two triangular prism-like members 64, 66 towards the base end side, the welding time: 2.0 minutes.

Drilling Step

Figure 13:
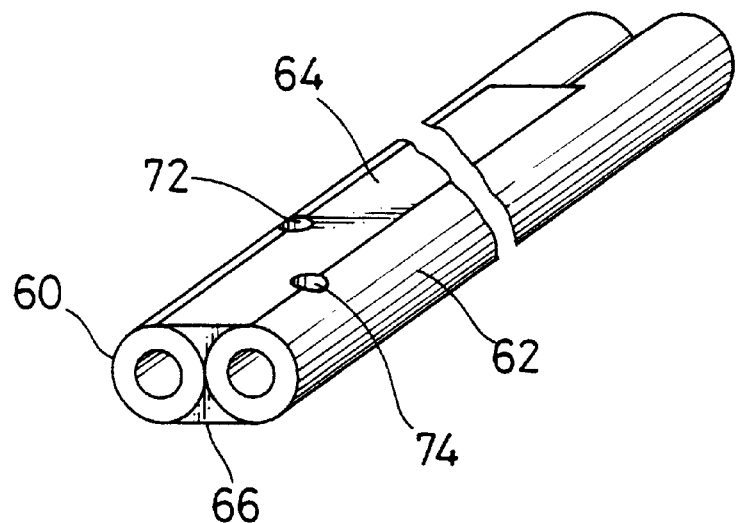
FIG. 13 is a construction view of the drilling step in manufacturing the sample sucking pipe of FIG. 8.

Referring to FIG. 13, a sucking opening 72 and a venting opening 74 are formed by carrying out a step of forming a through-hole by drilling into the sidewalls of the two capillary pipes 60, 62 and the two triangular prism-like members 64, 66 integrated in this manner. These openings 72, 74 each have a diameter of 0.5 mm and are formed at locations where the right and left edges of the upper triangular prism-like members 64 are in contact with the two capillary pipes 60, 62.

Closing Step

Figure 14:
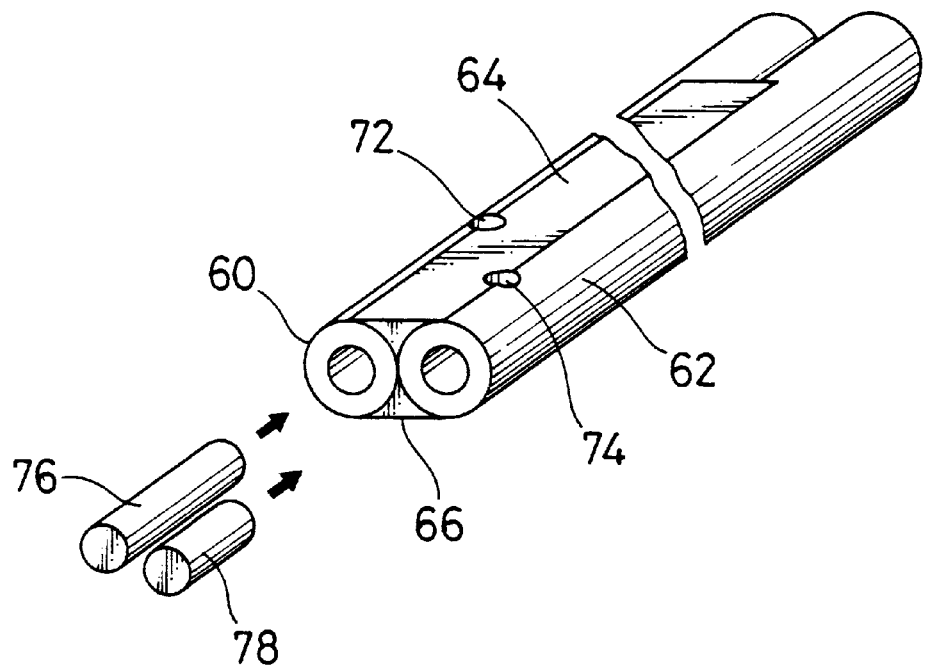
FIG. 14 is a construction view of the closing step in manufacturing the sample sucking pipe of FIG. 8.

Next, referring to FIG. 14, two long and short rod-like members (pins) 76, 78 made of the same stainless steel as that of the two capillary pipes 60, 62 and having a diameter of about 0.49 mm are respectively inserted into the unclosed capillary pipes 60, 62 from the tip end side to the edges of the openings 72, 74. The rod-like members 76, 78 to be inserted are preferably cooled to a predetermined temperature for carrying out the above-described cold fitting. After the insertion of these rod-like members 76, 78, the capillary pipes 60, 62 and the rod-like members 76, 78 are bonded by carrying out a spot welding onto the upper and lower surfaces (planes 64a, 66a) of the two triangular prism-like members 64, 66 and the right and left surfaces (sidewalls) of the two capillary pipes 60, 62 in the spot welding apparatus 100. This completes the closing of the tip end portions of the two capillary pipes 60, 62.

Grinding Step

Figure 15:
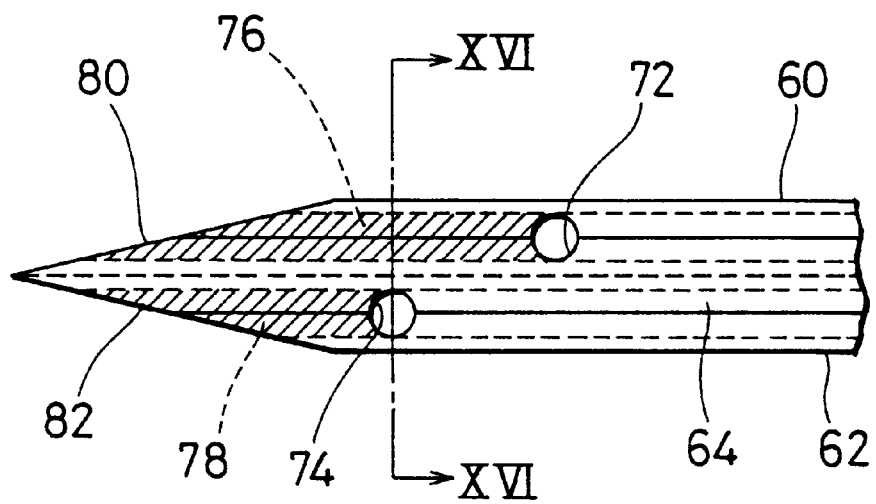
FIG. 15 is a construction view of the grinding step in manufacturing the sample sucking pipe of FIG. 8.

Subsequently, referring to FIG. 15, diagonal cut surfaces 80, 82 for piercing are formed by grinding the closed portions of the two capillary pipes 60, 62 to have sharpened edges. The grinding process and condition, and the size and shape of the diagonal cut surfaces 80, 82 are the same as those of the above-described sample sucking pipe P.

Coating Step

Then, the entire outer surface of the integrated capillary pipes 60, 62 and the triangular prism-like members 64, 66 is coated with a titanium film having a superior anti-abrasion and anti-corrosion property by means of ion-plating.

Step of Forming a Holding Piece

After carrying out the above steps, a holding piece (which is the same as the holding piece 30 of the sample sucking pipe P) is provided by means of polyacetal resin formation at the tip end side of the integrated capillary pipes 60, 62 to complete the sample sucking pipe Q.

Figure 16:
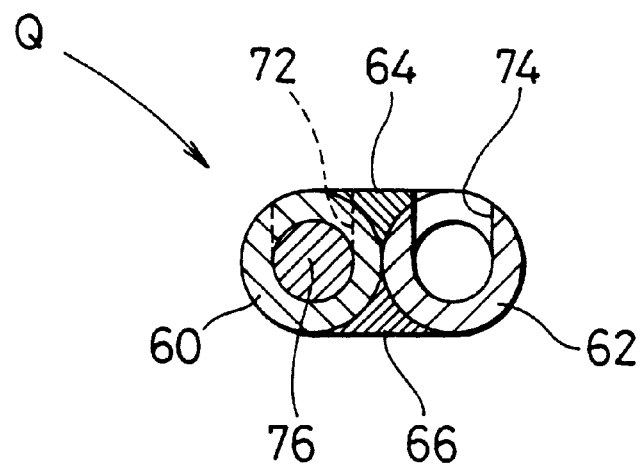
FIG. 16 is a sectional view along the line XVI—XVI of FIG. 15.

Referring to FIG. 16, the transversal cross section of the completed sample sucking pipe Q is substantially like an ellipse having no unevenness (roughness). Therefore, the sample sucking pipe Q is superior in strength and causes less friction when piercing the cap C of the sample vessel T.

Moreover, the two capillary pipes 60, 62 will not be bent in the manufacturing process because the spot welding is carried out by disposing electrodes on opposite sides of the two capillary pipes 60, 62 as shown above.

What is claimed is:

1. A sample sucking pipe structure adapted to pierce through a cap of a sample vessel both to vent the vessel and to suck a portion of a sample in the vessel the sucking structure comprising:

a first metal pipe for sucking having a closed portion at a tip end of its pipe passageway and a non-closed portion of its pipe passageway serving as a sample passageway and having in its wall a side-facing sucking opening communicating with the sample passageway;

a second metal pipe for venting having a closed portion at a tip end of its pipe passageway and a non-closed portion of its pipe passageway serving as a venting passageway and having in its wall a side-facing venting opening communicating with the venting passageway;

the first and second pipes disposed parallel to and in contact with each other and bonded together to form an integrated pipe unit, and having diagonal cut surfaces formed at a tip end of the integrated pipe for piercing the vessel cap; and each of the sucking opening and the venting opening disposed in a location shifted from a generatrix of the associated pipe extending from an end of the major axis of the diagonal cut surface of the associated pipe.

2. A sample sucking pipe structure according to claim 1, wherein the two pipes are both made of the same material and the closed portion is formed by inserting a rod-like member made of the same material into the tip end and bonding.

3. A sample sucking pipe structure according to claim 1, wherein the diagonal cut surfaces form a cap piercing point at a tip end of the unified tip portion and extend from the piercing point along the respective closed pipe tip portions for a selected extent, and the diagonal cut surfaces are peripherally displaced about the integrated pipe unit relative to respective peripheral positions of the side-facing sucking and venting openings.

4. A sample sucking pipe structure according to claim 3 wherein the diagonal cut surfaces are disposed back-to-back.

5. A sample sucking pipe structure according to claim 3, wherein the diagonal cut surfaces are formed substantially in symmetry.

6. A sample sucking pipe structure according to claim 1, wherein each of the sucking opening and the venting opening is disposed on a generatrix of the associated pipe extending from an end of the minor axis of the diagonal cut surface of the associated pipe.

7. A sample sucking pipe structure according to claim 1, further comprising two triangular prism-like members formed of the same material as the two pipes, wherein each of the triangular prism-like members includes a concave curved surface having substantially the same curvature as a side wall of one of the pipes and a concave curved surface having substantially the same curvature as a side wall of the other of the pipes, the two curved surfaces being adjacent to each other at a ridgeline, and the two triangular prism-like members are arranged along and in close contact with the two pipes at a sidewall of at least a tip end portion of the pipes with the ridgelines of the triangular prism-like members facing each other and are integrated with the pipes by bonding, whereby a transversal cross section of at least the tip end portion of the sample sucking pipe is shaped substantially like an ellipse.

8. A sample sucking pipe structure according to claim 1, wherein the bonding is performed by electric resistance welding.

* * * * *